(12) United States Patent
Jiang (10) Patent No.: US 9,869,776 B2
(45) Date of Patent: Jan. 16, 2018

(54) RAY DETECTOR

(71) Applicant: Boe Technology Group Co., Ltd., Beijing (CN)

(72) Inventor: Feng Jiang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/518,576

(22) PCT Filed: Jan. 4, 2016

(86) PCT No.: PCT/CN2016/070006
§ 371 (c)(1),
(2) Date: Apr. 12, 2017

(87) PCT Pub. No.: WO2017/028477
PCT Pub. Date: Feb. 23, 2017

(65) Prior Publication Data
US 2017/0285185 A1    Oct. 5, 2017

(30) Foreign Application Priority Data
Aug. 14, 2015    (CN) .......................... 2015 1 0498841

(51) Int. Cl.
*G01T 1/20* (2006.01)
*A61B 6/00* (2006.01)

(52) U.S. Cl.
CPC .............. *G01T 1/2018* (2013.01); *A61B 6/42* (2013.01); *G01T 1/2002* (2013.01)

(58) Field of Classification Search
CPC ........ A61B 6/42; G01T 1/2002; G01T 1/2018
See application file for complete search history.

(56) References Cited

U.S. PATENT DOCUMENTS

2002/0036267 A1    3/2002  Ikeda et al.
2003/0178623 A1    9/2003  Nishiki et al.
(Continued)

FOREIGN PATENT DOCUMENTS

CN    1365448 A    8/2002
CN    1447295 A    10/2003
(Continued)

OTHER PUBLICATIONS

Search Report for International Application No. PCT/CN2016/070006 dated Apr. 18, 2016.
(Continued)

*Primary Examiner* — Mark R Gaworecki
(74) *Attorney, Agent, or Firm* — Calfee, Halter & Griswold LLP (57) ABSTRACT

Embodiments of the disclosure provide a ray detector, which comprises a ray conversion layer for converting a ray incident on the ray detector into visible light, a photoelectric conversion layer for receiving the visible light and converting it into a charge signal, a pixel array having a plurality of pixels for detecting the charge signal, and a substrate below the photoelectric conversion layer, at least for directly or indirectly carrying the photoelectric conversion layer. The photoelectric conversion layer is made from a two-dimensional semiconductor material. Due to the high carrier mobility of the two-dimensional semiconductor material, it is possible to enable the external signal processing system to detect the charge signal more easily, so that a ray source with low energy can be used for ray detection. Therefore, a ray detector with high sensitivity can be provided, which may reduce the usage cost and be advantageous to saving energy.

12 Claims, 3 Drawing Sheets

(56) References Cited

U.S. PATENT DOCUMENTS

| | | |
|---|---|---|
| 2004/0262497 A1 | 12/2004 | Tokuda et al. |
| 2007/0096647 A1 | 5/2007 | Choo et al. |
| 2008/0128630 A1 | 6/2008 | Nomura et al. |
| 2008/0164473 A1 | 7/2008 | Tai et al. |
| 2012/0038013 A1 | 2/2012 | Karim et al. |
| 2012/0193542 A1 | 8/2012 | Yamada |
| 2016/0336373 A1 | 11/2016 | Gao et al. |

FOREIGN PATENT DOCUMENTS

| | | |
|---|---|---|
| CN | 101159283 A | 4/2008 |
| CN | 101221994 A | 7/2008 |
| CN | 102623466 A | 8/2012 |
| CN | 102664184 A | 9/2012 |
| CN | 103219403 A | 7/2013 |
| CN | 103296035 A | 9/2013 |
| CN | 103762251 A | 4/2014 |
| CN | 103803651 A | 5/2014 |
| CN | 104078508 A | 10/2014 |
| CN | 104218045 A | 12/2014 |
| CN | 104637970 A | 5/2015 |
| CN | 104795419 A | 7/2015 |
| CN | 105093259 A | 11/2015 |
| JP | 2004015000 A | 1/2004 |
| JP | 2005116543 A | 4/2005 |
| WO | 2004090996 A1 | 10/2004 |

OTHER PUBLICATIONS

First Office Action for Chinese Patent Application No. 201510498841.4 dated May 4, 2017.

Zhesheng, Chen et al., "A High performance graphene/few-layer InSe photo-dector," Nanoscale, 2015, 7, pp. 5981-5986.

Zhang, Yong, "Optoelectronic Properties of Single Layer MoS2 Semiconductor Materials," Jun. 2014, p. 18-25, published in China.

RAY DETECTOR

RELATED APPLICATIONS

The present application is the U.S. national phase entry of PCT/CN2016/070006, with an international filling date of Jan. 4, 2016, which claims the benefit of Chinese Patent Application NO. 201510498841.4, filed on Aug. 14, 2015, the entire disclosure of which is incorporated herein by reference.

FIELD OF THE INVENTION

The present disclosure relates to the field of ray detection technologies, and particularly to a ray detector.

BACKGROUND

Ray detectors are widely applied in various fields including medicine, industrial production and manufacturing, and so on, which can be used, for example, for physical examination, workpiece crack detection, etc. Modern ray detection techniques have been able to convert a ray signal to be detected into an image or photograph that can be displayed directly on a screen.

However, the existing ray detector typically employs a silicon-based PIN diode as the photosensitive element, but such silicon-based PIN diode material lacks toughness. Moreover, the carrier mobility of the silicon-based PIN diode is not high enough, so that the sensitivity of the resulting ray detector is not large enough. As a result, a ray source with very high intensity is required, resulting in a high cost of using the ray detector.

SUMMARY

Embodiments of the present disclosure provide ray detectors different from the prior art to alleviate or mitigate the above-mentioned problems.

A ray detector provided by an embodiment of the disclosure may comprise a ray conversion layer for converting a ray incident on the ray detector into visible light, a photoelectric conversion layer for receiving the visible light and converting the visible light into a charge signal, a pixel array having a plurality of pixels for detecting the charge signal, and a substrate below the photoelectric conversion layer, at least for directly or indirectly carrying the photoelectric conversion layer. The photoelectric conversion layer is made from a two-dimensional semiconductor material.

Compared with a conventional silicon-based PIN diode, the carrier mobility of the two-dimensional semiconductor material is higher, which means that the electron-hole pairs can be more easily excited to allow an external signal processing system to detect the charge signal more easily, so that a ray source with low energy can be used for ray detection. Thus, the ray detector provided by the embodiment has a relatively higher sensitivity, which makes the usage cost for the ray detector low and is advantageous to saving energy.

In an embodiment, the substrate in the ray detector may be a flexible substrate. In the conventional ray detector design, a hard material such as a glass substrate is often used as the base of the detection device. Such a ray detection device is cumbersome, which is inconvenient for the use and maintenance. Moreover, due to the use of a hard material as the base, the detection device is not easily bendably adjusted according to the shape of the object to be scanned, so that the result of ray detection is less accurate. In addition, since the existing ray detectors use a silicon-based PIN diode as the photosensitive element, such silicon-based PIN diode material lacks toughness and can not adapt to bending, which hampers the realization of a ray detector whose shape is adjustable.

The two-dimensional semiconductor material has good photoelectric performance, and only has a thickness of a few atomic layers. Therefore, compared with the photosensitive element such as a conventional silicon-based PIN diode, the thickness of the photoelectric conversion layer made from a two-dimensional semiconductor material is much smaller. Moreover, the photoelectric conversion layer thus formed also has good toughness and its characteristics are less liable to change upon bending. Therefore, the photoelectric conversion layer made from a two-dimensional semiconductor material provides the possibility of realizing a bendable ray detector. At the same time, with the bendable flexible substrate instead of a conventional substrate made from hard material, the resulting ray detector can be bent as a whole, in this way, the detection device can be bendably adjusted in accordance with the shape of the object to be scanned and can better contact the object to be scanned, making the result of ray detection more accurate. Meanwhile, the detection device becomes light and convenient, which facilitates the usage and maintenance.

In addition, the transmittance of the two-dimensional semiconductor material is relatively high. Therefore, the ray detectors comprising the photoelectric conversion layer made from the two-dimensional semiconductor material as provided by embodiments of the disclosure are not limited to receiving rays from a single direction. Instead, ray detectors having different structures may be designed. For example, the ray detector may be designed to receive rays from above, or may be designed to receive rays from below, which can achieve upper and lower double-sided sensing of the ray source. Therefore, forming the photoelectric conversion layer with the two-dimensional semiconductor material enables a larger variance in the structural design of the ray detector.

In the ray detector according to an embodiment of the present disclosure, each pixel in the pixel array may comprise a pixel switch, a pixel electrode, and a common electrode. The pixel electrode may be electrically connected to a source or a drain of the pixel switch, and the common electrode and the pixel electrode are in contact with the photoelectric conversion layer. When the ray detector is in operation, the ray conversion layer can convert the rays incident on a surface of the ray detector into visible light, the photoelectric conversion layer can convert the visible light into a charge signal, and the pixel electrode can gather the charge signal generated by the photoelectric conversion layer. When the pixel switch electrically connected to the pixel electrode is turned on, the pixel switch may transmit the charge signal to a signal processing system to further process the charge signal to form an image or picture.

In another embodiment, the ray detector may further comprise a first intermediate layer adjacent to the ray conversion layer, the first intermediate layer comprising a light blocking matrix and a first passivation layer. The first passivation layer may be formed on the same layer as the light blocking matrix and formed between the light blocking matrices to provide protection for the photoelectric conversion layer. Alternatively, the first passivation layer may cover the light blocking matrix. The light blocking matrix can define the photosensitive region of the ray detector, and can alleviate the mutual crosstalk of the light emitted by the ray conversion layer portions to which the adjacent pixels correspond to increase the resolution of the ray detector, thereby improving the accuracy of ray detection.

In embodiments, the pixel array, the photoelectric conversion layer, the first intermediate layer, and the ray conversion layer may be formed successively on the flexible substrate from bottom to top so as to realize a ray detector capable of receiving rays from above.

Alternatively, in a further embodiment, the ray detector may comprise a second intermediate layer adjacent to the ray conversion layer, and the second intermediate layer may comprise only a light blocking matrix.

Further, in another embodiment, the ray detector may further comprise a third intermediate layer for protecting the photoelectric conversion layer. The third intermediate layer is above the photoelectric conversion layer and is in contact with the photoelectric conversion layer, and each pixel electrode is electrically connected to the source or the drain of each pixel switch through a via hole in the third intermediate layer.

In such an embodiment, the photoelectric conversion layer, the third intermediate layer, and the pixel array may be formed successively on a first surface of the flexible substrate from bottom to top, and the second intermediate layer and the ray conversion layer may be formed successively on a second surface of the flexible substrate opposite to the first surface from top to bottom, thereby realizing a ray detector capable of receiving rays from below.

In an embodiment, the third intermediate layer may be made from silicon oxynitride.

In the ray detectors provided by the embodiments of the present disclosure, the two-dimensional semiconductor materials for forming the photoelectric conversion layer may include molybdenum disulfide or indium selenide.

In addition, the ray conversion layer may be formed using different materials capable of converting different rays into visible light. The ray detectors provided by embodiments of the present disclosure can be used to detect different rays including X-rays.

In the ray detectors provided by the various embodiments, the flexible substrate may be made from one or more of the following materials: polyethylene naphthalate, polyethylene terephthalate, and polytetrafluoroethylene.

According to another aspect of the present disclosure, there is provided a method of manufacturing a photoelectric conversion layer capable of receiving visible light and converting the visible light into a charge signal. The method may comprise the steps of:

sprinkling powders of a two-dimensional semiconductor material uniformly on a friction substrate;

rubbing the friction substrate using a first flexible board to obtain a friction substrate attached with the two-dimensional semiconductor material;

rubbing the friction substrate attached with the two-dimensional semiconductor material against a target substrate to form the photoelectric conversion layer on the target substrate.

The method of forming the photoelectric conversion layer as mentioned above may be referred to herein as a "rubbing transfer deposition process". As described above, utilizing a two-dimensional semiconductor material to form the photoelectric conversion layer in the ray detector can improve the sensitivity of the ray detector and reduce the cost of using the ray detector. In addition, the method does not require a high temperature condition, and the deposition area of the deposited two-dimensional semiconductor material may depend on the size of the rubbed region. Therefore, with this process, a large-area photoelectric conversion layer can be prepared at low temperatures. Thus, such a method of manufacturing a ray detector reduces the requirement on the temperature condition of the process and improves the efficiency of the manufacturing process.

Further, in another embodiment, the method of forming the photoelectric conversion layer may further comprise, after rubbing the friction substrate using a first flexible board, rubbing the friction substrate attached with the two-dimensional semiconductor material using a second flexible board. In this way, a two-dimensional semiconductor material layer having a better adhesion and a finer surface can be obtained on the friction substrate.

In the above-described method of manufacturing the photoelectric conversion layer, the friction substrate may include an abrasive paper or a polishing disc.

Embodiments of the present disclosure further provide a method of manufacturing a ray detector. The method may comprise the following steps: forming, over a substrate, a pixel array comprising a plurality of pixels and a photoelectric conversion layer; forming a ray conversion layer for converting rays incident on the ray detector into visible light; the photoelectric conversion layer is formed by means of the method of forming the photoelectric conversion layer as mentioned in the above embodiment, and the photoelectric conversion layer is for receiving the visible light and converting the visible light into a charge signal. Utilizing this method to manufacture a ray detector can reduce the requirement on the temperature condition of the process and improve the efficiency of the manufacturing process. Meanwhile, this helps to improve the sensitivity of the manufactured ray detector and reduce the cost of using the manufactured ray detector.

Further, the substrate is a flexible substrate. By using the bendable characteristic of the flexible substrate in combination with the characteristics of the photoelectric conversion layer made from the two-dimensional semiconductor material, it is possible to enable the ray detector to be bendably adjustable integrally in accordance with the shape of the object to be scanned, and to better contact the object to be scanned, making the result of ray detection more accurate. Meanwhile, the detection device becomes light and convenient, which facilitates the use and maintenance.

In an embodiment, the target substrate on which the photoelectric conversion layer is to be formed is a flexible substrate on which the pixel array has been formed, and the photoelectric conversion layer and the ray conversion layer are formed successively over the pixel array.

Further, the step of forming the pixel array comprises fabricating a common electrode and a pixel electrode corresponding to each pixel, the common electrode and the pixel electrode being in contact with the photoelectric conversion layer.

Further, the method of manufacturing a ray detector further comprises the step of forming a first intermediate layer on the photoelectric conversion layer after forming the photoelectric conversion layer, the first intermediate layer comprising a light blocking matrix and a passivation layer.

Alternatively, the target substrate may be the flexible substrate, in this case, the photoelectric conversion layer and the pixel array are formed successively on the flexible substrate, and the ray conversion layer is formed below the flexible substrate.

Further, the step of forming the pixel array comprises forming a common electrode and a pixel electrode corresponding to each pixel on the formed photoelectric conversion layer.

Further, the method of manufacturing a ray detector may further comprise the step of forming, after forming the pixel electrode and the common electrode, a third intermediate layer for protecting the photoelectric conversion layer. Each pixel electrode is electrically connected to the source or drain of the pixel switch in each pixel through a via hole in the third intermediate layer.

Further, the method of manufacturing a ray detector may further comprise the step of forming a second intermediate layer below the flexible substrate prior to manufacturing the ray conversion layer, and the second intermediate layer comprising a light blocking matrix.

As for the ray detector provided by embodiments of the present disclosure or the ray detector formed by the method of manufacturing a ray detector as provided by embodiments of the present disclosure, the sensitivity of the ray detector is improved such that the external signal processing system can detect the charge signal more easily, thus a ray source with low energy can be used for ray detection. Thus, the ray detector provided by the present embodiment has high sensitivity, which makes the cost of using the ray detector low and is advantageous to saving energy.

BRIEF DESCRIPTION OF THE DRAWINGS

Embodiments of the present disclosure are described in more detail by way of non-limiting example with reference to the accompanying drawings, in which FIG. 1 schematically shows a cross-sectional view of a ray detector according to an embodiment of the present disclosure which receives rays from above.

DETAILED DESCRIPTION OF EMBODIMENTS

Specific embodiments of the invention will be described below in detail by way of example. It is to be understood that the embodiments of the invention are not limited to the examples set forth below, and those skilled in the art can make modifications and variations to the illustrated embodiments using the principle or spirit of the present disclosure to obtain other embodiments in different forms. Obviously, these embodiments all fall within the scope of the invention.

A ray detector according to an embodiment of the disclosure may comprise a ray conversion layer for converting rays incident on the ray detector into visible light, a photoelectric conversion layer for receiving the visible light and converting the visible light into a charge signal, a pixel array having a plurality of pixels for detecting the charge signal, and a substrate below the photoelectric conversion layer which is configured to at least directly or indirectly carry the photoelectric conversion layer. The photoelectric conversion layer is made from a two-dimensional semiconductor material.

The ray conversion layer may be a thin film that receives rays incident on the ray detector and converts the received rays into visible light. For example, the thin film may convert X-rays irradiated thereon into visible light, and in this case the thin film may be made from a phosphor or a cesium iodide (CsI) material. Alternatively, such a thin film may also be formed using other materials having similar functions, for example, gadolinium oxysulfide phosphor ($Gd_2O_2S$:Tb), tin sulfide (ZnS), cadmium tungstate ($CdWO4$), and the like. If X-rays are incident on the thin film, the thin film layer may fluoresce. Of course, it is to be understood that the ray detector provided by embodiments of the disclosure can also detect other rays, such as γ-rays, and accordingly, the ray conversion layer may be made from different materials capable of converting different rays into visible light. Since the two-dimensional semiconductor material has good photoelectric performance, the photoelectric conversion layer made from the two-dimensional semiconductor material can receive the visible light emitted by the ray conversion layer when the ray detector is in operation, and convert the received visible light into a charge signal. Moreover, the pixel electrode in the pixel may gather the charge signal so that the generated charge signal can be detected. Thereafter, the charge signal can be transmitted by the pixel switch in the pixel to a signal processing system outside the ray detector and converted by the signal processing system into an image signal. The substrate below the photoelectric conversion layer may be at least used for directly or indirectly carrying the photoelectric conversion layer to support the respective layer structures disposed thereon.

Since the two-dimensional semiconductor material has a relatively large carrier mobility, it enables the external signal processing system to detect the charge signal more easily, so that a ray source with relatively low energy can be used for ray detection. Thus, the ray detector provided by the embodiment has relatively high sensitivity, which makes the cost of using the ray detector low and is advantageous to saving energy.

In another embodiment, the substrate may be a flexible substrate. Due to the usage of a flexible substrate rather than a conventional glass substrate, the overall weight of the ray detector is reduced to facilitate the use or maintenance. Meanwhile, the two-dimensional semiconductor material typically only has a thickness of several atomic layers, thus the thickness of the photoelectric conversion layer made from the two-dimensional semiconductor material which is used as the photosensitive element is much smaller than the thickness of the conventional silicon-based PIN diode. In this way, the photoelectric conversion layer may have a good toughness, whose characteristics are not easy to change upon bending. Thus, the overall bending for the ray detector can be realized so that the detection device can be bendably adjusted in accordance with the shape of the object to be scanned to better contact the object to be scanned, making the result of the ray detection more accurate.

In various embodiments of the present disclosure, any suitable material may be used to form the respective layers. For example, the flexible substrate may be formed with polyester materials including, but not limited to, polyethylene naphthalate (PEN), polyethylene terephthalate (PET), polytetrafluoroethylene (PTEF), and the like. The two-dimensional semiconductor materials that form the photoelectric conversion layer include, but not limited to, molybdenum disulfide (MoS2), indium selenide (InSe), and the like.

Embodiments of the ray detector of the disclosure can be more clearly illustrated by way of schematic drawings.

Figure 1:
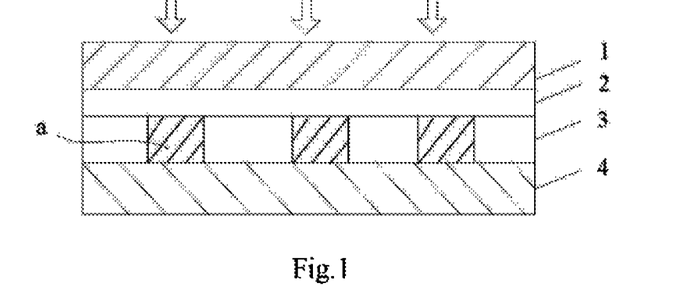

For example, FIG. 1 schematically shows a cross-sectional view of a ray detector according to an embodiment of the present disclosure. The ray detector may comprise a ray conversion layer 1, a photoelectric conversion layer 2, a pixel array 3 having a plurality of pixels a, and a substrate 4 below the photoelectric conversion layer 2. Likewise, the photoelectric conversion layer 2 may be made from a two-dimensional semiconductor material. In this embodiment, the substrate 4 is below the photoelectric conversion layer 2, but does not directly carry the photoelectric conversion layer 2. The pixel array 3 is arranged between the photoelectric conversion layer 2 and the substrate 4, and the substrate 4 serves as a base plate in this case, which can support the ray conversion layer 1, the photoelectric conversion layer 2, and the pixel array 3 simultaneously. In the embodiment shown in FIG. 1, as shown by the arrows in FIG. 1, the rays may be incident on the ray detector from above, in other words, the front surface of the ray detector may serve as the surface that receives the rays. In addition, it can be understood by those skilled in the art that the pixel a shown schematically in FIG. 1 is not a cross-sectional view of an actual pixel structure, and the plurality of pixels a as shown are merely used to represent the structural relationships between the pixel array and the photoelectric conversion layer 2 as well as the substrate 4.

Figure 2:
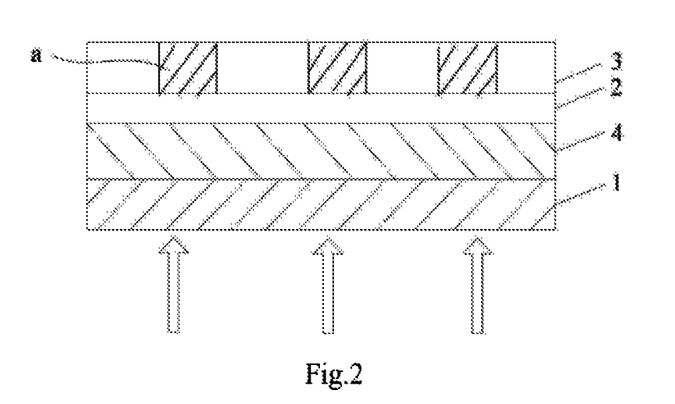
FIG. 2 schematically shows a cross-sectional view of a ray detector according to another embodiment of the present disclosure which receives rays from below.

Alternatively, in another embodiment, as shown in FIG. 2, the substrate 4 is below the photoelectric conversion layer 2 and may directly carry the photoelectric conversion layer 2. The pixel array 3 including a plurality of pixels a may be formed on the photoelectric conversion layer 2, and the ray conversion layer 1 may be disposed below the flexible substrate 4. As shown by the arrows in FIG. 2, in this case, the rays may be incident on the ray detector from below, or the bottom surface of the ray detector may serve as the surface that receives the rays. Likewise, it can be understood by those skilled in the art that the pixel a shown schematically in FIG. 2 is not a cross-sectional view of an actual pixel structure, and the plurality of pixels a as shown are merely used to represent the structural relationship between the pixel array and the photoelectric conversion layer 2.

The two-dimensional semiconductor material has a relatively high transmittance. Therefore, in different embodiments of the present disclosure, the ray detector may be not only designed to receive the rays from above, but also designed to receive the rays from below, which may achieve double-sided sensing of the rays from ray source. The ray detector may be designed to have various structures.

Figure 3:
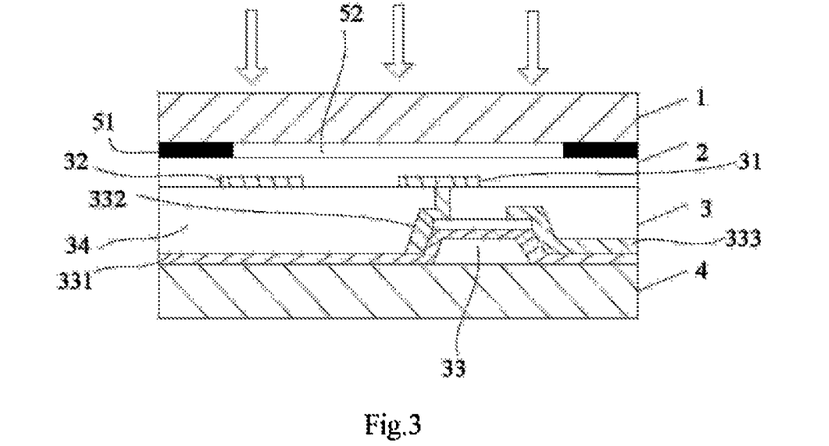
FIG. 3 schematically shows a cross-sectional view of a ray detector according to another embodiment of the present disclosure.

Each pixel in the pixel array of the ray detector may include a pixel switch, a pixel electrode, and a common electrode. The pixel electrode may be electrically connected to the drain or source of the pixel switch, and the common electrode and the pixel electrode may be in contact with the photoelectric conversion layer. For example, FIG. 3 schematically shows a cross-sectional view of a ray detector according to another embodiment of the present disclosure, and in FIG. 3, a schematic structural diagram of a single pixel in the pixel array is shown. Each pixel in the pixel array may include a pixel switch 33, a pixel electrode 31, and a common electrode 32. It is to be understood that a single pixel electrode 31 corresponds to a single pixel switch 33, and all the pixels in the pixel array may share a common electrode 32 which may be a planar electrode. In this embodiment, the pixel electrode 31 may be electrically connected to a source 332 of the pixel switch, and the common electrode 32 and the pixel electrode 31 may be in contact with the photoelectric conversion layer 2. When the ray converter is in operation, the photoelectric conversion layer 2 converts the visible light from the ray conversion layer 1 into a charge signal. The charge may be accumulated onto the pixel electrode 31 under the effect of the electric field between the pixel electrode 31 and the common electrode 32, and the accumulated charge can be transferred to the source 332 of the pixel switch 33. Thus, the pixel switch 33 can detect the charge signal so that the charge signal can be transmitted to an external signal processing system when the pixel switch 33 is turned on and further converted to an image or picture signal. In other embodiments, the pixel electrode 31 may be electrically connected to a drain 333 of the pixel switch. Of course, the pixel switch 33 may also comprise other structures well known to those skilled in the art, such as a gate, a gate insulating layer 331, and so on, which are not described here for simplicity. In the embodiment shown in FIG. 3, the pixel switch may be a thin film transistor (TFT), and the pixel array can be formed with the flexible substrate 4, obtaining a so-called TFT array substrate. It can be understood by those skilled in the art that the pixel switch 33 may be formed as a back channel etching (BCE) structure in addition to the pixel switch in the form of an etching stop layer (ESL) structure as shown in FIG. 3. In the embodiment of FIG. 3, the pixel array 3 further comprises a passivation layer 34 covering the pixel switch 33 of each pixel. The passivation layer 34 may protect the pixel switch 33 and may planarize the pixel array 3 comprising the respective pixels.

In various embodiments of the present disclosure, a molybdenum aluminum alloy may be used as the material for the pixel electrode or the common electrode. For such material, the resistivity is small, and the degree of element diffusion is low, which are advantageous to the stability of the manufactured switch devices.

In another embodiment, the ray detector may further comprise a first intermediate layer adjacent to the ray conversion layer, and the first intermediate layer may comprise a light blocking matrix and a first passivation layer. The ray detector according to this embodiment can be specifically described with reference to FIG. 3 again. As shown in FIG. 3, the first intermediate layer adjacent to the ray conversion layer 1 may comprise a light blocking matrix 51 and a first passivation layer 52. The light blocking matrix 51 may be a pattern made from a material capable of reflecting or absorbing light, which can define the photosensitive region of the ray detector. For example, the light blocking matrix 51 may be a black matrix. The black matrix can be made from a polymer material, and can be manufactured by depositing a pattern using an inkjet printing process. Adverse effects of the etchant used in the conventional photolithography process on the two-dimensional semiconductor material can be avoided as compared to the conventional photolithography process.

Figure 4:
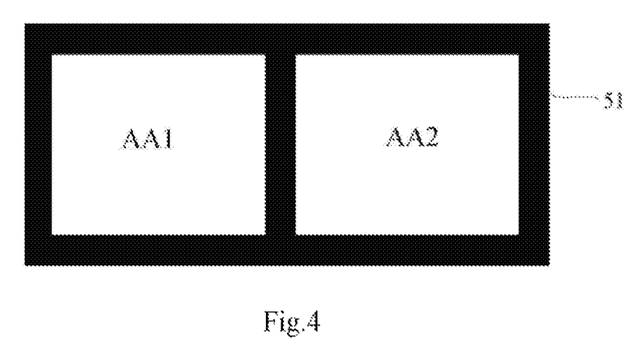
FIG. 4 schematically shows the situation that a light blocking matrix in the ray detector defines the photosensitive regions according to another embodiment of the present disclosure.

FIG. 4 schematically shows the light blocking matrix 51 that defines two photosensitive regions AA1 and AA2, each of which may comprise one pixel. When the ray detector is in operation, the visible light emitted by the ray conversion layer 1 under the irradiation of the rays may be emitted from all directions. Therefore, it is very likely that the light emitted from the ray conversion layer corresponding to each or several pixels reaches the photoelectric conversion layer corresponding to the adjacent pixel, this light is also converted into charges by the photoelectric conversion layer corresponding to the adjacent pixel, and the charges are accumulated on the pixel electrode of the adjacent pixel. As a result, the resolution may be reduced, affecting the accuracy of ray detection. Therefore, by providing the light blocking matrix 51, it is possible to alleviate the mutual crosstalk of the light emitted from the ray conversion layer portion to which the adjacent pixels correspond and increase the resolution of the ray detector, thereby improving the accuracy of ray detection. The first passivation layer 52 may be a transparent protective layer made from silicon oxynitride material, which may block water and oxygen for the photoelectric conversion layer 2 so as to protect the photoelectric conversion layer 2. The first passivation layer 52 may correspond to the photosensitive regions defined by the light blocking matrix 51 as shown in FIG. 3, and in other embodiments the first passivation layer 52 may also cover the light blocking matrix 51.

Therefore, in the ray detector according to another embodiment of the present disclosure, the pixel array 3, the photoelectric conversion layer 2, the first intermediate layer and the ray conversion layer 1 can be formed successively on the substrate 4 from the bottom to the top. In this way, a ray detector which receives rays from above can be realized, which has relatively high sensitivity and can be bent according to the object to be scanned. Furthermore, since the crosstalk phenomenon is alleviated or suppressed such that the resolution is increased, the accuracy of ray detection can be further improved.

Figure 5:
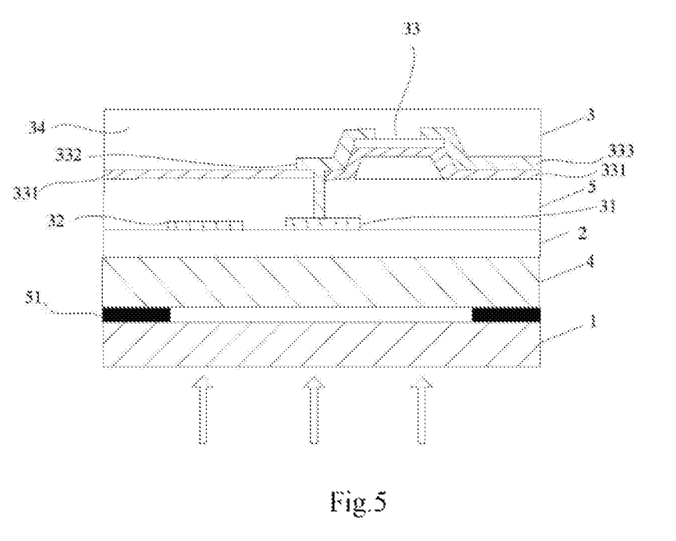
FIG. 5 schematically shows a cross-sectional view of a ray detector according to a further embodiment of the present disclosure.

FIG. 5 schematically shows a cross-sectional view of a ray detector according to a further embodiment of the present disclosure. In this embodiment, the ray detector may further comprise a second intermediate layer adjacent to the ray conversion layer 1, and the second intermediate layer may comprise a light blocking matrix 51. The light blocking matrix 51 may define the photosensitive regions of the ray detector and have the same function or effect as the light blocking matrix in the foregoing embodiment, which is not repeated herein. Likewise, each pixel in the pixel array 3 may comprise a pixel switch 33, a pixel electrode 31, and a common electrode 32. The pixel electrode 31 may be electrically connected to the source or drain of the pixel switch 33, and the common electrode 32 and the pixel electrode 31 may be in contact with the photoelectric conversion layer 2. The pixel array 3 may further comprise a passivation layer 34 that covers the pixel switch 33 of each pixel so as to protect the pixel switch 33 and planarize the pixel array 3 comprising respective pixels.

Further, in yet another embodiment, the ray detector may further comprise a third intermediate layer for protecting the photoelectric conversion layer. The third intermediate layer is above the photoelectric conversion layer and in contact with the photoelectric conversion layer, and the pixel electrode of each pixel may be electrically connected to the source or drain of the pixel switch via a via hole in the third intermediate layer. Here, this embodiment may be described with reference to FIG. 5 again. As shown in FIG. 5, the third intermediate layer 5 is located above the photoelectric conversion layer 2 and in contact with the photoelectric conversion layer 2, and the pixel electrode 31 of each pixel may be electrically connected to a source 332 of the pixel switch 33 via a via hole in the third intermediate layer 5. In this embodiment, the third intermediate layer 5 may be made from an organic or inorganic material having water and oxygen barrier performance so as to protect the photoelectric conversion layer 2. Such material includes but is not limited to silicon oxynitride.

Therefore, in another embodiment of the ray detector according to the present disclosure, the photoelectric conversion layer 2, the third intermediate layer 5, and the pixel array 3 may be formed successively on a first surface of the flexible substrate 4 from bottom to top, and the second intermediate layer and the ray conversion layer 1 may be formed successively on a second surface of the flexible substrate 4 opposite to the first surface from top to bottom. In this way, a ray detector which receives rays from below can be realized, which has relatively high sensitivity and can be bent according to the object to be scanned. Furthermore, since the crosstalk phenomenon is alleviated or suppressed such that the resolution is increased, the accuracy of ray detection can be further improved.

In the actual manufacturing process of the ray detector, the photoelectric conversion layers 2 in the ray detectors of the above embodiments can be prepared by different methods or processes. A conventional method may employ a direct chemical vapor deposition (CVD) process, i.e., a two-dimensional semiconductor material is deposited directly on a target substrate using a chemical vapor deposition (CVD) process. However, this process has a high requirement on the temperature, the temperature may reach 600-800 degrees C., and it may be difficult for the flexible substrate to withstand such high temperatures. This process is not suitable for manufacturing the photoelectric conversion layer in the ray detector of the present disclosure. The photoelectric conversion layer may be prepared by a flexible board transfer method. In particular, a two-dimensional semiconductor material may be deposited on a metal foil using a chemical vapor deposition (CVD) process, the metal foil is then eroded to obtain an independent two-dimensional semiconductor material thin film, and then the two-dimensional semiconductor material is transferred onto a flexible board. Thereafter, the flexible board may be flip-fitted to a surface of the target substrate (e.g., the surface of the pixel array 3 in which the common electrode 32 and the pixel electrode 31 have been formed as shown in FIG. 3). In this case, the flexible board may also serve as a water and oxygen barrier layer for the two-dimensional semiconductor material. However, this method of preparing the photoelectric conversion layer has a certain limitation, which is suitable for the preparation of a small-area two-dimensional semiconductor material layer and is not suitable for the preparation of a large-area two-dimensional semiconductor material layer.

Another method of manufacturing a photoelectric conversion layer may employ a rubbing transfer deposition process, which may comprise the following steps: uniformly sprinkling powders of a two-dimensional semiconductor material onto a friction substrate, rubbing the friction substrate using a first flexible board to obtain a friction substrate attached with the two-dimensional semiconductor material, and rubbing the friction substrate attached with the two-dimensional semiconductor material against a target substrate to form a photoelectric conversion layer on the target substrate. The resulting photoelectric conversion layer is capable of receiving visible light and converting the visible light into a charge signal. The target substrate is not uniquely selected and may correspond to the appropriate structures that have been formed in the ray detector. For example, when the photoelectric conversion layer 2 in the ray detector shown in FIG. 5 is to be prepared, the target substrate may be the substrate of the ray detector, or when the photoelectric conversion layer 2 in the ray detector shown in FIG. 3 is to be prepared, the target substrate may be the substrate on which a pixel array has been formed.

As described above, utilizing a two-dimensional semiconductor material to form the photoelectric conversion layer in the ray detector can improve the sensitivity of the ray detector and reduce the usage cost for the ray detector. In addition, this rubbing transfer deposition process does not require a high temperature condition, and the deposition area of the deposited two-dimensional semiconductor material may depend on the size of the rubbed region. Therefore, with this process, a large-area photoelectric conversion layer can be prepared at low temperatures.

Figure 6:
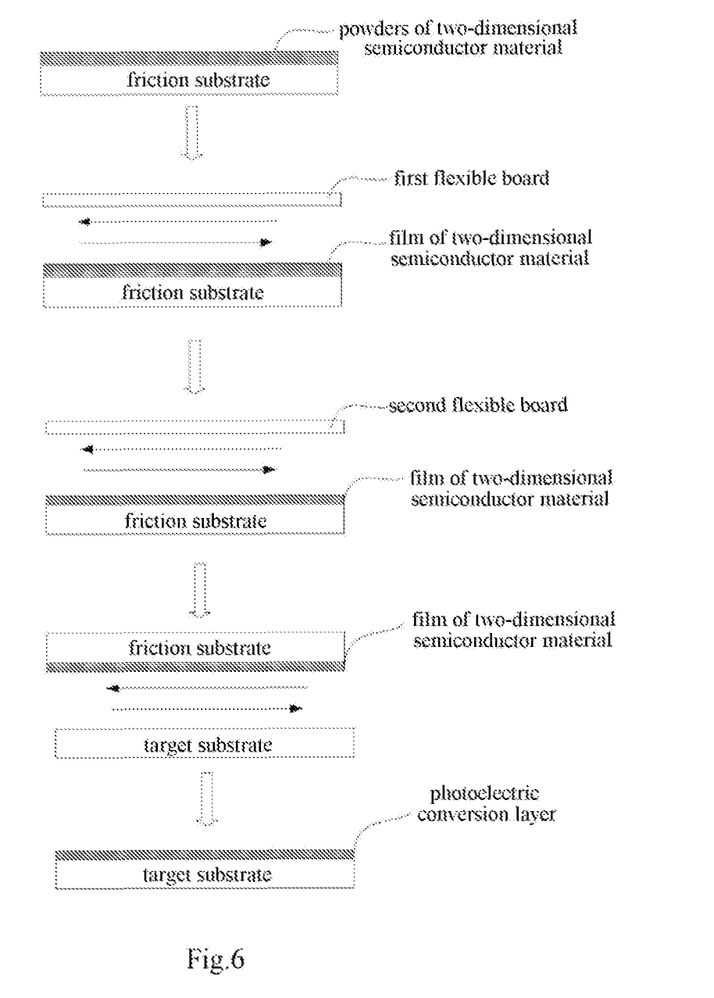
FIG. 6 schematically shows an example of a method of forming a photoelectric conversion layer in the ray detectors provided by the embodiments of the present disclosure.

In another embodiment, the method of forming the photoelectric conversion layer may further comprise the step of rubbing the friction substrate attached with the two-dimensional semiconductor material using a second flexible board after rubbing the friction substrate with the first flexible board. This makes it possible to obtain a two-dimensional semiconductor material layer having a better adhesion and a finer surface on the friction substrate. Thereafter, the friction substrate attached with the two-dimensional semiconductor material is then rubbed against the target substrate so as to form a photoelectric conversion layer on the target substrate. The formation process of such a photoelectric conversion layer can be schematically shown in FIG. 6.

The above-mentioned friction substrate may be a hard substrate such as an abrasive paper or a polishing disc, and the first flexible board and the second flexible board may be smooth flexible thin films.

Another embodiment of the present disclosure provides a method of manufacturing a ray detector. The method comprises the following steps: forming, over a substrate, a pixel array comprising a plurality of pixels and a photoelectric conversion layer, and forming a ray conversion layer for converting rays incident on the ray detector into visible light. The photoelectric conversion layer can be formed by the method of forming a photoelectric conversion layer as provided by any of the embodiments described above, and the photoelectric conversion layer is used for receiving the visible light and converting the visible light into a charge signal. Manufacturing a ray detector using such a method can reduce the requirement on temperatures conditions of the process, and can improve the efficiency of the manufacturing process. At the same time, manufacturing the photoelectric conversion layer using a two-dimensional semiconductor material helps to improve the sensitivity of the manufactured ray detector and reduce the usage cost for the manufactured ray detector.

In another embodiment, the substrate may be a flexible substrate. By means of the bendable characteristic of the flexible substrate in combination with the characteristics of the photoelectric conversion layer made from the two-dimensional semiconductor material, it is possible to enable the ray detector to be bendably adjustable integrally in accordance with the shape of the object to be scanned, and to better contact the object to be scanned, such that the result of ray detection is more accurate. Meanwhile, the detection device becomes light and convenient, which facilitates the usage and maintenance.

In an embodiment, the target substrate on which the photoelectric conversion layer is to be formed may be a flexible substrate on which the pixel array has been formed, and the photoelectric conversion layer and the ray conversion layer are formed successively over the pixel array. In this way, a ray detector which receives rays from above can be realized, which has relatively high sensitivity and can be bent according to the object to be scanned, thereby further improving the accuracy of ray detection.

Further, the step of forming the pixel array may comprise: fabricating a common electrode and a pixel electrode corresponding to each pixel. The common electrode and the pixel electrode are in contact with the photoelectric conversion layer.

Further, the method of manufacturing a ray detector further comprises the steps of manufacturing a first intermediate layer on the photoelectric conversion layer after forming the photoelectric conversion layer. The first intermediate layer comprises a light blocking matrix and a passivation layer.

Alternatively, the target substrate may be the flexible substrate, the photoelectric conversion layer and the pixel array are formed successively on the flexible substrate, and the ray conversion layer is formed below the flexible substrate. Likewise, a ray detector which receives rays from below can be realized, which has relatively high sensitivity and can be bent according to the object to be scanned, thereby further improving the accuracy of ray detection. Further, the step of forming the pixel array comprises forming a common electrode and a pixel electrode corresponding to each pixel on the formed photoelectric conversion layer.

Further, the method of manufacturing the ray detector may further comprise the step of forming, after forming the pixel electrode and the common electrode, a third intermediate layer for protecting the photoelectric conversion layer. Each pixel electrode is electrically connected to the source or drain of the pixel switch in each pixel through a via hole in the third intermediate layer.

Further, the method of manufacturing a ray detector may further comprise the step of forming a second intermediate layer below the flexible substrate prior to manufacturing the ray conversion layer. The second intermediate layer comprises a light blocking matrix.

The various embodiments of the method as described above have similar technical effects as the foregoing embodiments of the ray detector, which are not described here in detail.

It is to be noted that the above-described embodiments are intended to illustrate rather than limiting the invention, and that those skilled in the art will be able to design many alternative embodiments without departing from the scope of the appended claims. In the claims, the word "comprising" does not exclude elements or steps other than those recited in the claims, and the indefinite article "a" or "an" does not exclude a plurality. The mere fact that certain measures are recited in mutually different dependent claims does not indicate that a combination of these measures cannot be used to advantage.

The invention claimed is:

1. A method of manufacturing a photoelectric conversion layer capable of receiving visible light and converting the visible light into a charge signal, wherein the method comprises:
    sprinkling powders of a two-dimensional semiconductor material uniformly on a friction substrate;
    rubbing the friction substrate using a first flexible board to obtain a friction substrate attached with the two-dimensional semiconductor material;
    rubbing the friction substrate attached with the two-dimensional semiconductor material against a target substrate to form the photoelectric conversion layer on the target substrate.

2. The method according to claim 1, wherein the method further comprises rubbing the friction substrate attached with the two-dimensional semiconductor material using a second flexible board after rubbing the friction substrate with the first flexible board.

3. The method according to claim 2, the friction substrate comprising an abrasive paper or a polishing disc.

4. A method of manufacturing a ray detector, wherein the method comprises:
forming, above a substrate, a pixel array comprising a plurality of pixels and a photoelectric conversion layer;
forming a ray conversion layer for converting a ray incident on the ray detector into visible light;
wherein the photoelectric conversion layer is used for receiving the visible light and converting the visible light into a charge signal,
and wherein forming the photoelectric conversion layer comprises the steps of:
sprinkling powders of a two-dimensional semiconductor material uniformly on a friction substrate;
rubbing the friction substrate using a first flexible board to obtain a friction substrate attached with the two-dimensional semiconductor material;
rubbing the friction substrate attached with the two-dimensional semiconductor material against a target substrate to form the photoelectric conversion layer on the target substrate.

5. The method of manufacturing a ray detector according to claim 4, wherein the substrate is a flexible substrate.

6. The method of manufacturing a ray detector according to claim 5, wherein the target substrate is a flexible substrate on which the pixel array has been formed, the photoelectric conversion layer and the ray conversion layer being formed successively over the pixel array.

7. The method of manufacturing a ray detector according to claim 6, wherein a step of forming the pixel array comprises: manufacturing a common electrode and a pixel electrode corresponding to each pixel, the common electrode and the pixel electrode being in contact with the photoelectric conversion layer.

8. The method of manufacturing a ray detector according to claim 7, wherein the method further comprises manufacturing a first intermediate layer on the photoelectric conversion layer after forming the photoelectric conversion layer, the first intermediate layer comprising a light blocking matrix and a passivation layer.

9. The method of manufacturing a ray detector according to claim 5, wherein the target substrate is the flexible substrate, the photoelectric conversion layer and the pixel array being formed successively on the flexible substrate, the ray conversion layer being formed below the flexible substrate.

10. The method of manufacturing a ray detector according to claim 9, wherein the step of forming the pixel array comprises manufacturing a common electrode and a pixel electrode corresponding to each pixel on the formed photoelectric conversion layer.

11. The method of manufacturing a ray detector according to claim 10, wherein the method further comprises forming a third intermediate layer for protecting the photoelectric conversion layer after forming the pixel electrode and the common electrode, each pixel electrode being electrically connected to a source or a drain of a pixel switch in each pixel through a via hole in the third intermediate layer.

12. The method of manufacturing a ray detector according to claim 11, wherein the method further comprises steps of:
forming a second intermediate layer below the flexible substrate prior to manufacturing the ray conversion layer, the second intermediate layer comprising a light blocking matrix.

\* \* \* \* \*